United States Patent
Koch et al.

(10) Patent No.: US 7,835,793 B2
(45) Date of Patent: Nov. 16, 2010

(54) INSERT MOLDED SHROUD FOR IMPLANTABLE PLATE-TYPE ELECTRODES

(75) Inventors: Alexandra M. Koch, Golden Valley, MN (US); Steven J. Fischer, Star Prairie, MN (US); Alexander O. Lakanu, Marietta, GA (US); Bryan J. Zart, Shakopee, MN (US)

(73) Assignee: Medtronic, Inc., Minneapolis, MN (US)

( * ) Notice: Subject to any disclaimer, the term of this patent is extended or adjusted under 35 U.S.C. 154(b) by 560 days.

(21) Appl. No.: 11/669,391

(22) Filed: Jan. 31, 2007

(65) Prior Publication Data

US 2008/0183233 A1     Jul. 31, 2008

(51) Int. Cl.
*A61N 1/00* (2006.01)
(52) U.S. Cl. ......................................... 607/36
(58) Field of Classification Search ............ 607/36
See application file for complete search history.

(56) References Cited

U.S. PATENT DOCUMENTS

| | | | |
|---|---|---|---|
| 3,983,867 A | 10/1976 | Case | |
| 4,023,565 A | 5/1977 | Ohlsson | |
| 4,082,086 A | 4/1978 | Page et al. | |
| 4,121,576 A | 10/1978 | Greensite | |
| 4,170,227 A | 10/1979 | Feldman et al. | |
| 4,263,919 A | 4/1981 | Levin | |
| 4,310,000 A | 1/1982 | Lindemans | |
| 4,313,443 A | 2/1982 | Lund | |
| 4,506,680 A | 3/1985 | Stokes | |
| 4,593,702 A | 6/1986 | Kepski et al. | |
| 5,331,966 A | 7/1994 | Bennett et al. | |
| 5,443,778 A * | 8/1995 | Schlingman | 264/257 |
| 5,522,861 A * | 6/1996 | Sikorski et al. | 607/36 |
| 6,205,358 B1 | 3/2001 | Haeg et al. | |
| 6,522,915 B1 | 2/2003 | Ceballos et al. | |
| 6,975,906 B2 * | 12/2005 | Rusin et al. | 607/36 |
| 6,997,949 B2 | 2/2006 | Tuch | |
| 2003/0069612 A1 * | 4/2003 | Zart et al. | 607/36 |
| 2006/0217777 A1 | 9/2006 | Strom et al. | |
| 2006/0217778 A1 | 9/2006 | Strom et al. | |

FOREIGN PATENT DOCUMENTS

WO    WO0236000 A    5/2002

\* cited by examiner

*Primary Examiner*—Mark W Bockelman
*Assistant Examiner*—Elizabeth K So
(74) *Attorney, Agent, or Firm*—Stephen W. Bauer; Reed A. Duthler

(57) ABSTRACT

Apparatus and method for fabricating a shroud member having extra-cardiac sensing electrode. The assembly is used to provide a subcutaneous cardiac activity sensing device via at least a pair of electrodes mechanically coupled to the shroud member. In one embodiment only a major surface portion of the electrodes are exposed to body fluid and tissue. One beneficial aspect of the fabrication techniques herein involve the encapsulation of the elongated conductors and a majority of the electrode surfaces thereby reducing possibility for electrical shorting among the IMD housing and the other conductive members. The assemblies provided can be fabricated efficiently, inexpensively, quickly and easily using insert-molding techniques.

20 Claims, 6 Drawing Sheets

INSERT MOLDED SHROUD FOR IMPLANTABLE PLATE-TYPE ELECTRODES

CROSS REFERENCE TO RELATED APPLICATIONS

The present patent document is related to co-pending non-provisional patent applications; namely, Ser. No. 11/085,843, entitled, "APPARATUS AND METHODS OF MONITORING CARDIAC ACTIVITY UTILIZING IMPLANTABLE SHROUD-BASED ELECTRODES," filed on 22 Mar. 2005 and Ser. No. 11/380,811 entitled, "SHROUD-BASED ELECTRODES HAVING VENTED GAPS," filed 28 Apr. 2006, the contents of which are hereby fully incorporated by reference herein.

FIELD OF THE INVENTION

The present invention relates generally to implantable medical devices (IMDs) and more particularly to a subcutaneous multiple electrode sensing and recording system for acquiring electrocardiographic data and waveform tracings from an implanted medical device without the need for or use of surface (skin) electrodes. More particularly, the present invention relates to implantable devices that are equipped with a shroud member fabricated via insert molding whereby the electrodes and, as applicable elongated conductors, are placed in a mold cavity prior to injecting biocompatible medical grade resin therein.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. For example, S-T segment changes can be used to detect an ischemic episode. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

Previous art describes how to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems, which combine surface EKG signals for artifact rejection.

The primary use for multiple electrode systems in the prior art is vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

With regard to various aspects of time-release of surface coatings and the like for chronically implanted medical devices, the following issued patents are incorporated herein by reference. U.S. Pat. Nos. 6,997,949 issued 14 Feb. 2006 and entitled, "Medical device for delivering a therapeutic agent and method of preparation," and 4,506,680 entitled, "Drug dispensing body implantable lead." In the former patent, the following is described (from the Abstract section of the '949 patent) as follows: A device useful for localized delivery of a therapeutic agent is provided. The device includes a structure including a porous polymeric material and an elutable therapeutic agent in the form of a solid, gel, or neat liquid, which is dispersed in at least a portion of the porous polymeric material. Methods for making a medical device having blood-contacting surface electrodes is also provided.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG. Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY

The present invention provides a leadless subcutaneous (or submuscular) single or multiple-electrode array that provides various embodiments of a compliant surround shroud coupled to a peripheral portion of an implantable medical device (IMD). The shroud incorporates a plurality of substantially planar electrodes mechanically coupled within recessed portions of the shroud. These electrodes electrically couple to circuitry of an IMD and are adapted to detect cardiac activity of a subject. Temporal recordings of the detected cardiac activity are referred to herein as an extra-cardiac electrogram (EC-EGM). The recordings can be stored upon computer readable media within an IMD at various resolution (e.g., continuous beat-by-beat, periodic, triggered, mean value, average value, etc.). Real time or stored EC-EGM signals can be provided to remote equipment via telemetry. For example, when telemetry, or programming, head of an IMD programming apparatus is positioned within range of an IMD the programmer receives some or all of the EC-EGM signals.

Certain embodiments of the invention utilize a substantially planar sensing surface for the electrodes. According to the invention, the electrodes—and attendant elongated conductors—are inserted into position within the cavity of a mold the shroud portion of the electrode array. Following injection of a mold-injectable biocompatible material the mold is cooled and the shroud assembly removed. The assembly is characterized by protruding end portions of the conductors which are then suitable coupled to opposing ends of conductors of circuitry within the IMD.

In one embodiment, the injectable material comprises a clear material thereby improving quality control inspection of the molded articles. In another aspect, the exposed major planar surface of the electrodes is covered with a protective coating or layer of material that can be optionally removed following fabrication of the shroud.

The present invention thus provides improved apparatus and methods for reliably collecting EC-EGM signals for use or collection in conjunction with diverse IMDs (e.g., implantable pacemakers having endocardial leads, implantable cardioverter-defibrillators or ICDs, drug delivery pumps, subcutaneous ICDs, submuscular ICDs, brain stimulation devices, nerve stimulation devices, muscle stimulation devices and the like).

The invention can be implemented employing suitable sensing amplifiers, switching circuits, signal processors, and memory to process the EC-EGM signals collected between any selected pair or pairs of the electrodes deployed in an array around the periphery or surface of a housing of an IMD to provide a leadless, orientation-insensitive means for receiving the EC-EGM signals from the heart.

The shroud can comprise a non-conductive, bio-compatible material such as any appropriate resin-based material, urethane polymer, silicone, or relatively soft urethane that retains its mechanical integrity during manufacturing and prolonged exposure to body fluids. The shroud placed around the peripheral portions of an IMD can utilize a number of configurations (e.g., two, three, four recesses) for individual electrodes. However, a three-electrode embodiment appears to provide an improved signal-to-noise ratio than other configurations. And, embodiments having a single electrode pair appear much more sensitive to appropriate orientation of the device relative to the heart than embodiments having more than a single pair of electrodes. Of course, embodiments of the invention using more than four electrodes increase complexity without providing a significant improvement in signal quality.

Embodiments having electrodes connected to three sense-amplifiers that are hardwired to three electrodes can record simultaneous EC-EGM signals. Alternative embodiments employ electrodes on the face of the lead connector, or header module, and/or major planar face(s) of the pacemaker that may be selectively or sequentially coupled in one or more pairs to the terminals of one or more sense amplifiers to pick up, amplify and process the EC-EGM signals across each electrode pair. In one aspect, the EC-EGM signals from a first electrode pair are stored and compared to other electrode pair(s) in order to determine the optimal sensing vector. Following such an optimization procedure, the system can be programmed to chronically employ the selected subcutaneous EC-EGM signal vector.

With respect to the elongated conductor coupling the planar electrodes to operative circuitry within an IMD, the assembly includes a unitary member stamped from a plate of conductive material such as titanium. In one embodiment the unitary member comprises a pre-shaped partially serpentine workpiece having a slightly curvilinear (i.e., substantially planar) major plate portion, a transition portion, and a partially serpentine portion adapted to cooperate with the configuration of the pre-configured conductor pathway.

Electrode assemblies according to the invention can be used for chronic or acute EC-EGM signal sensing collection and attendant heart rate monitoring, capture detection, arrhythmia detection, and the like as well as detection of myriad other cardiac insults (e.g., ischemia monitoring using S-T segment changes, pulmonary edema monitoring based upon impedance changes).

In addition, the surface of the electrode can be treated with one or more electrode coatings to enhance signal-conducting, de- and re-polarization sensing properties, and to reduce polarization voltages (e.g., platinum black, titanium nitride, titanium oxide, iridium oxide, carbon, etc.). That is the surface area of the electrode surfaces may be increased by techniques known in the art. and/or can be coated with such materials as just described and equivalents thereof. All of these materials are known to increase the true electrical surface area to improve the efficiency of electrical performance by reducing wasteful electrode polarization, among other advantages.

These and other advantageous aspects of the invention will be appreciated by those of skill in the art after studying the invention herein described, depicted and claimed. In addition, persons of skill in the art will appreciate insubstantial modifications of the invention that are intended to be expressly covered by the appended claims.

DETAILED DESCRIPTION OF THE DRAWINGS

Figure 1:
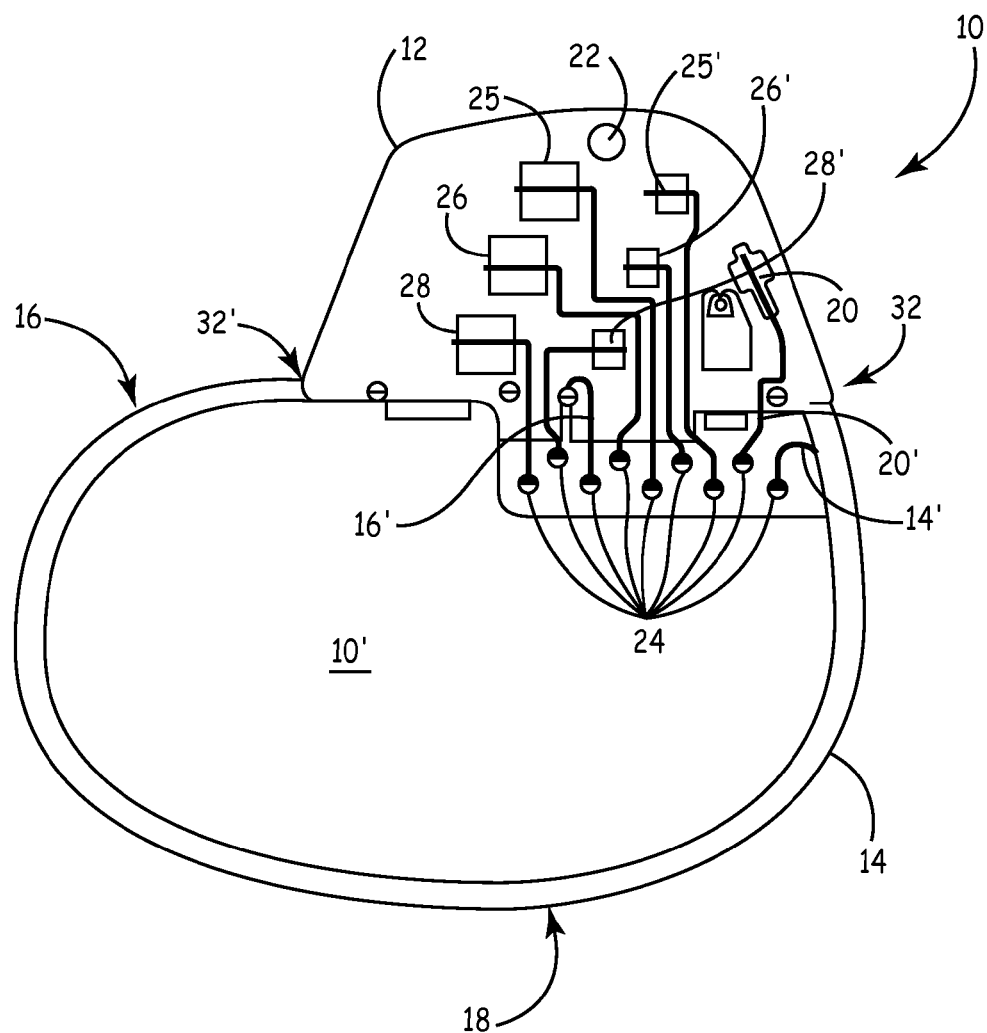
FIG. 1 is an elevational side view depicting an exemplary shroud assembly coupled to an IMD which illustrates electrical conductors disposed in the header, or connector, portion of the IMD which is configured to receive a proximal end portion of medical electrical leads (not shown).

FIG. 1 is an elevational side view depicting an exemplary shroud assembly 14 coupled to an IMD 10 which illustrates electrical conductors 24,25,26,28 disposed in the header, or connector, portion 12 of the IMD 10 which are configured to couple to end portions of medical electrical leads as well as couple to operative circuitry within the IMD housing (not shown). The shroud assembly 14 surrounds IMD 10 and mechanically couples to the header portion 12 and includes at least three discrete electrodes 16,18,20 adapted for sensing far-field, or extra-cardiac electrogram (EC-EGM) signals. FIG. 1 also depicts an aperture 22 formed within the header 12 which can be used to receive thread used to suture the header 12 (and thus the IMD 10) to a fixed surgical location (also known as a pocket) of a patient's body.

As partially depicted in FIG. 1, an elongated conductor 14' couples to electrode 14, elongated conductor 16' couples to electrode 16, and conductor segment 20' couples to electrode 20. Furthermore, three of the conductors (denoted collectively with reference numeral 24) couple to three cuff-type conductors 25,26,28 adapted to receive proximal portions of medical electrical leads while another three of the conductors couple to conductive pads 25',26',28' which are aligned with, but spaced from the conductors 25,26,28 along a trio of bores (denoted as 25",26",28" in FIG. 4 herein) formed in header 12.

Figure 2:
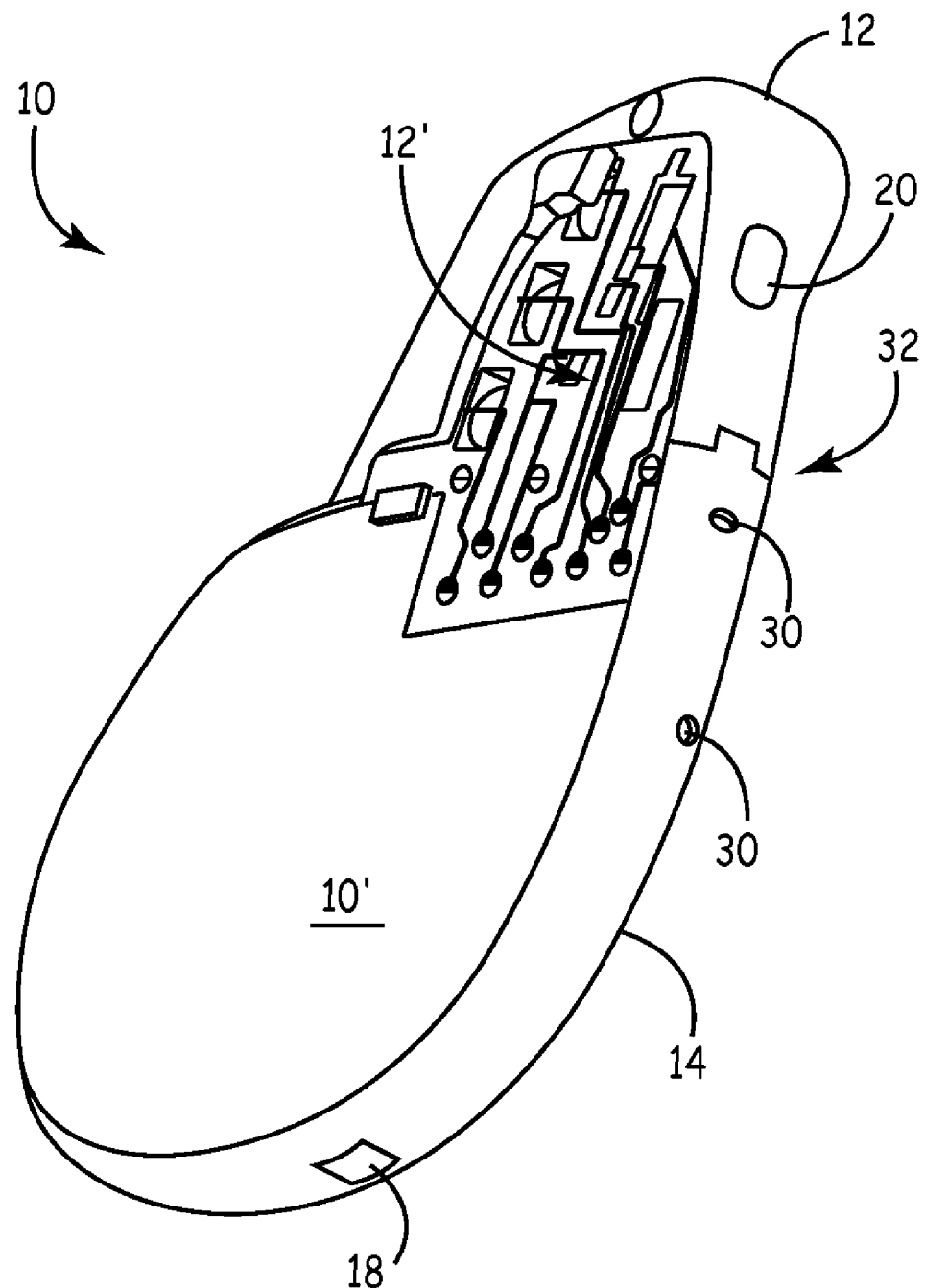
FIG. 2 is a perspective view of the IMD depicted in FIG. 1 further illustrating the shroud assembly.

FIG. 2 is a perspective view of the IMD 10 depicted in FIG. 1 further illustrating the shroud assembly 14 and two of the three electrodes 18,20. In addition, two of a plurality of adhesive ports 30 and a mechanical joint 32 between the elongated portion of the shroud assembly 14 and the header 12 are also depicted in FIG. 2. The ports 30 can be used to evacuate excess medical adhesive disposed between the shroud assembly 14 and the IMD 10 and/or used to inject medical adhesive into one or more ports 30 to fill the void(s) therebetween. In one form of the invention, a major lateral portion 12' of header 12 remains open to ambient conditions during assembly of the IMD 10. Subsequent to making electrical connections between the plurality of conductors of the shroud assembly 14 and the header 12, the open lateral portion 12' is sealed (e.g., automatically or manually filled with a biocompatible substance such as a substantially clear medical adhesive, such as Tecothane® made by Noveon, Inc. a wholly owned subsidiary of The Lubrizol Corporation). Thus most if not all of the plurality of conductors of the shroud assembly 14 and the IMD 10 are visible and can be manually and/or automatically inspected to ensure long term operability and highest quality of the completed IMD 10.

Some properties of various Tecothane® appear below (as published in the Technical Data Sheet (TDS) for certain clear grades of the material:

| Tecothane ® Typical Physical Test Data - CLEAR GRADES | | | | | | | | | |
|---|---|---|---|---|---|---|---|---|---|
| | ASTM Test | TT-1074A | TT-1086A | TT-1095A | TT-1066D | TT-1065D | TT-1069D | TT-1072D | TT-1076D-M |
| Durometer (Shore Hardness) | D2240 | 75A | 85A | 94A | 54D | 64D | 69D | 74D | 75D |
| Specific Gravity | D792 | 1.10 | 1.12 | 1.15 | 1.16 | 1.18 | 1.18 | 1.18 | 1.19 |
| Flexural Modulus (psi) | D790 | 1.300 | 3.000 | 8.000 | 19.000 | 26.000 | 44.000 | 73.000 | 180.000 |

-continued

Tecothane ® Typical Physical Test Data - CLEAR GRADES

| | ASTM Test | TT-1074A | TT-1086A | TT-1095A | TT-1066D | TT-1065D | TT-1069D | TT-1072D | TT-1076D-M |
|---|---|---|---|---|---|---|---|---|---|
| Ultimate Tensile (psi) | D412 | 6.000 | 7.000 | 9.000 | 9.600 | 10.000 | 8.800 | 9.000 | 8.300 |
| Ultimate Elongation (%) | D412 | 550 | 450 | 400 | 350 | 300 | 310 | 275 | 150 |
| Tensile (psi) | D412 | | | | | | | | |
| at 100% Elongation | | 500 | 800 | 1.300 | 2.500 | 2.800 | 3.200 | 3.700 | 3.600 |
| at 200% Elongation | | 700 | 1.000 | 2.100 | 3.800 | 4.600 | 4.200 | 3.900 | NA |
| at 300% Elongation | | 1.100 | 1.600 | 4.300 | 6.500 | 7.800 | NA | NA | NA |
| Melt Index (gm/10 min at 2160 gm load) | D1238 | 3.5 (205° C.) | 4.0 (205° C.) | 3.8 (210° C.) | 4.0 (210° C.) | 2.0 (210° C.) | 3.0 (210° C.) | 2.0 (210° C.) | 5.0 (210° C.) |
| Mold Shrinkage (in/in) | D955 | .008-.012 | .008-.012 | .086-.010 | .004-.008 | .004-.008 | .004-.008 | .004-.006 | .004-.006 |

Referring again to FIG. 2, the terminal ends of conductors 24 are depicted to include the optional shaped-end portion which provides a target for reliable automatic and/or manual coupling (e.g., laser welding, soldering, and the like) of the terminal end portions to respective conductive pins of a multipolar feedthrough assembly (not shown). As is known in the art, such conductive pins hermetically couple to operative circuitry disposed within the IMD 10.

Figure 3:
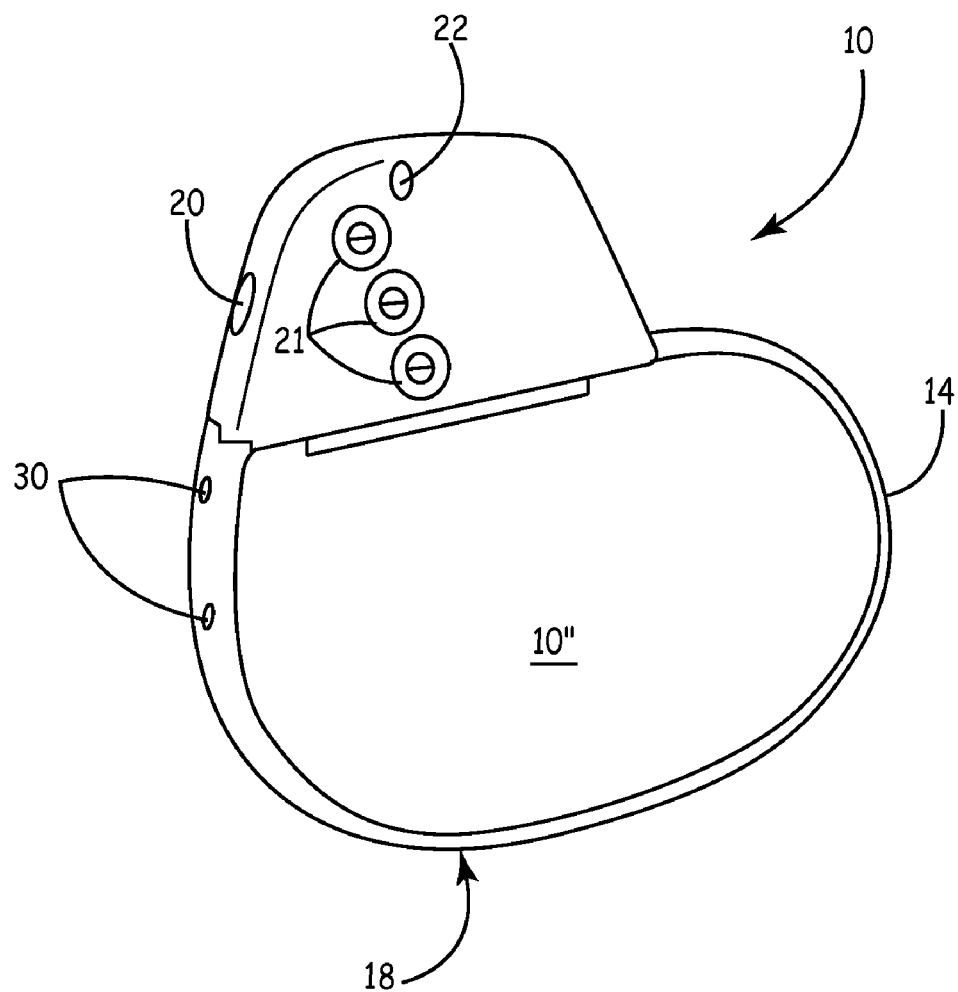
FIG. 3 is a perspective view of an opposing major side of the IMD depicted in FIGS. 1 and 2.
Figure 6:
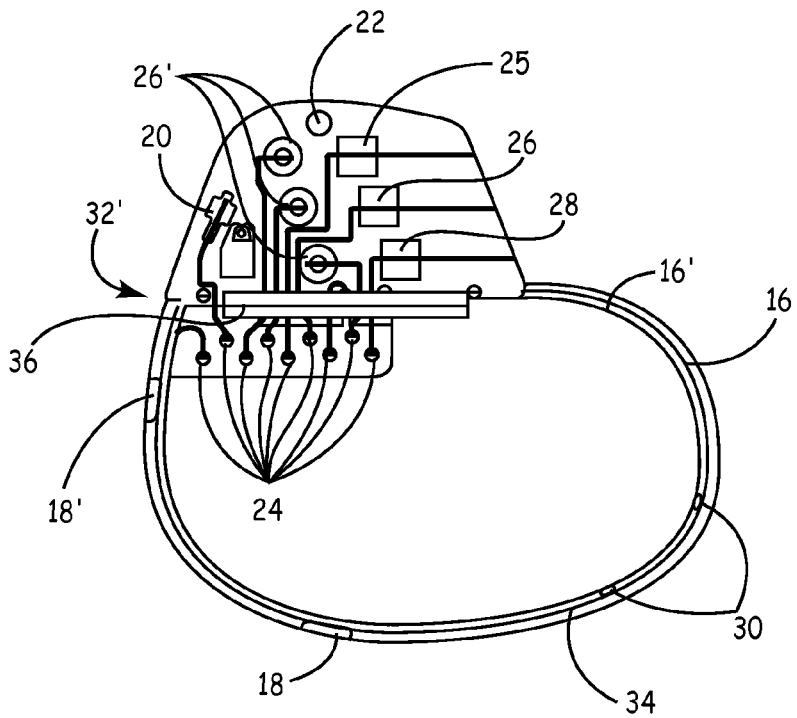
FIG. 6 is a view of a second side of the transparent shroud assembly coupled to a header according to the invention that clearly illustrates that the conductors and components of the assembly are readily visible from both sides.

FIG. 3 is a perspective view of an opposing major side 10'' of the IMD 10 depicted in FIGS. 1 and 2 and three self-healing grommets 21 substantially hermetically coupled to openings of a like number of threaded bores (shown in FIG. 6 and denoted by reference numeral 26'). As is known, the threaded bores are configured to receive a threaded shank and the grommets 21 are fabricated to temporarily admit a mechanical tool (not shown). The tool is used to connect and allow a physician or clinician to manually tighten the conductors 25,26,28, for example, with compression and/or radially around conductive rings disposed on proximal portions of medical electrical leads (not shown). In addition, two of the plurality of ports 30 are also depicted in FIG. 3.

Figure 4:
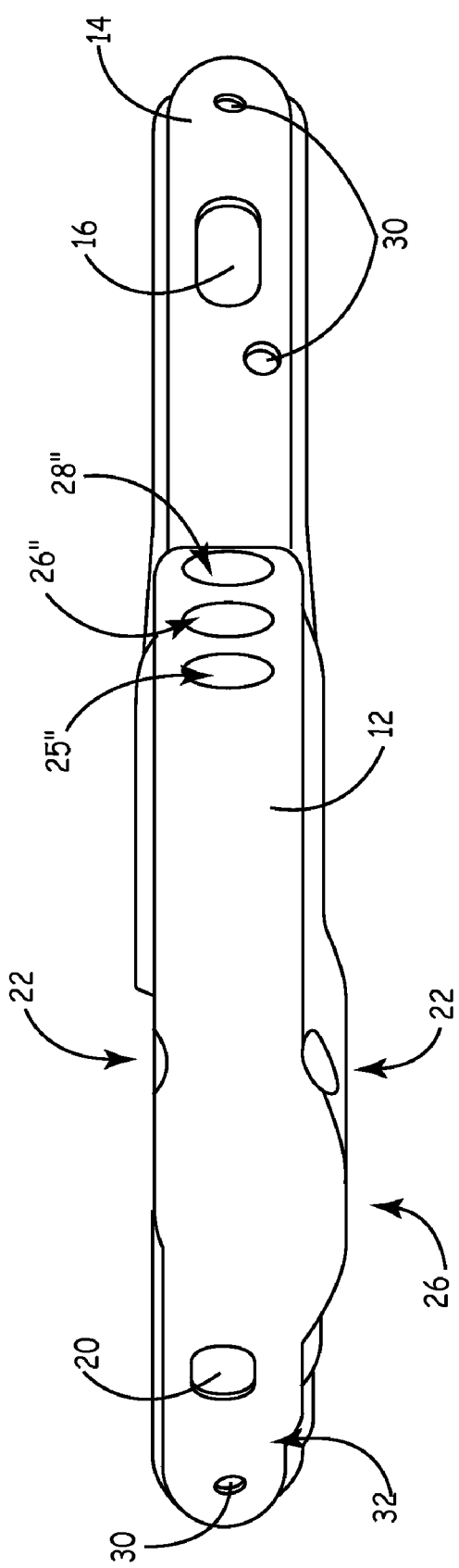
FIG. 4 is a plan view of the IMD previously depicted that illustrates the relationship between two of the electrodes coupled to the shroud assembly as well as depicting the header, or connector, of the IMD.

FIG. 4 is a plan view of the IMD 10 previously depicted that illustrates the relationship between two of the electrodes 16,20 coupled to the shroud assembly 14 as well as depicting the header 12, or connector, of the IMD 10. Opposing openings of the aperture 22 formed in the header 12 are also depicted in FIG. 4 as are the three openings 25'',26'',28'' of the bores or ports formed in the header 12 that are configured to admit the proximal end of medical electrical leads (not shown). Three of the adhesive-admitting ports 30 are shown distributed at various locations through the surfaces of the shroud 14.

Three elongated conductors individually couple to a respective electrode 14,16,18. These elongated conductors can be continuous or discrete segments of conductive material. In the event that they comprise discrete segments, they need to be coupled together such as with convention means like laser bonding, welding, soldering and the like. For example, the elongated conductor coupling to electrode 16 can traverse either direction around the periphery of the IMD 10 disposed within or mechanically coupled to an inner portion of the shroud 14. If it traverses past the seam 32 it might need to be isolated from the elongated conductor coupled to electrode 18 (assuming that conductor also traversed seam 32). If the conductor coupling electrode 16 is routed directly toward the header 12 (and the header/shroud is not a unitary structure) then a bond between segments of the elongated conductor could be necessary at the junction of the shroud 14 and the header 12.

Figure 5:
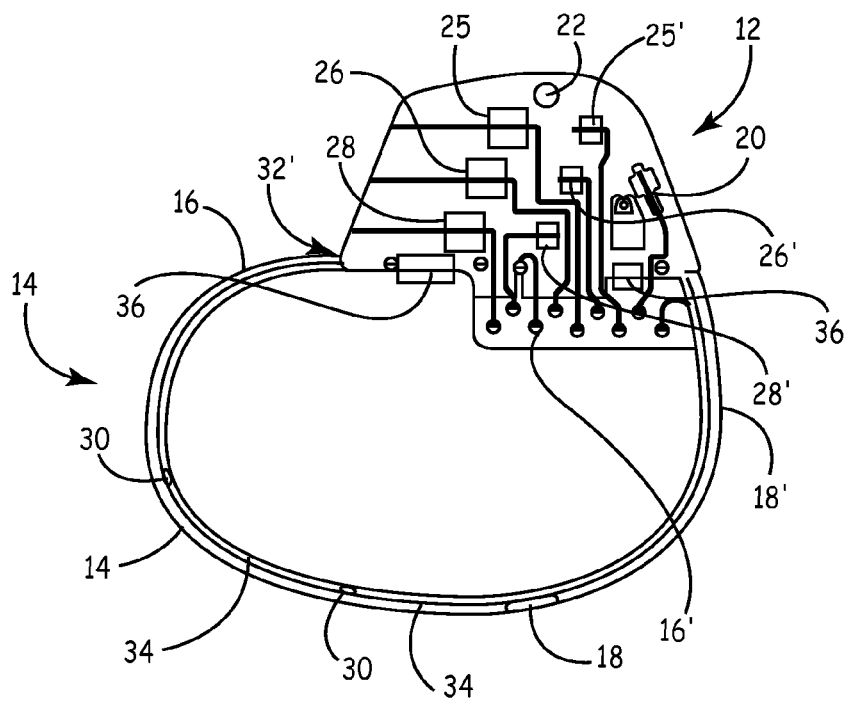
FIG. 5 is a view of a first side of a transparent shroud assembly coupled to a header according to the invention that clearly illustrates that the conductors and components of the assembly are readily visible.

FIG. 5 is a view of a first side of a transparent shroud assembly 14 coupled to a header 12 according to the invention that clearly illustrates that the conductors and components of the assembly are readily visible. FIG. 6 is a view of a second side of the transparent shroud assembly coupled to a header according to the invention that clearly illustrates that the conductors and components of the assembly are readily visible from both sides.

Since FIG. 5 and FIG. 6 essentially depict common components of the inventive assembly of the invention they shall be described together. The exemplary shroud assembly 14 of FIGS. 5 and 6 is depicted with an IMD 10 for clarity. The electrical conductors 25,26,28 disposed in the header, or connector, portion 12 of the IMD 10 are configured to couple to end portions of medical electrical leads as well as couple to operative circuitry within the IMD housing (not shown). The shroud assembly 14 mechanically couples to the header portion 12 at each end of the shroud assembly 14 both mechanically and electrically via medical adhesive (disposed at overlapping joint 32') and an elongate conductor 16' (passing through joint 32'). The three discrete electrodes 16,18,20 and their corresponding elongated conductors 16',18', 20' are coupled together. While not depicted in FIGS. 5 and 6 the conductors 16', 18', 20' have at least a partially serpentine configuration and conductors 16', 18' are furthermore mechanically coupled to the shroud with a series of elongated stand-off bosses 34. In addition, and as previously mentioned, during attachment to an IMD adhesive is disposed intermediate the shroud 14 and the IMD with excess being evacuated from ports 30 (and/or if needed injected into one of more ports 30) to eliminate any air bubbles. Of course, one feature of the invention relates to the ability to fully inspect the finished article visually (including the quality of the electrical connections and the quality of the bond between the shroud 14 and an IMD. Also, the electrodes 16, 18 can be at least one of mechanically embedded partially into the material of the shroud 14 and configured to receive medical adhesive to retain the electrodes in position (e.g., using perforated wing-like peripheral portions of the electrodes disposed at the ends, sides, and/or other parts of the periphery of an electrode). Aperture 22 also can be seen in FIGS. 5 and 6 formed in a peripheral portion of the header 12. Also depicted is how the elongated conductor 14' couples to electrode 14, elongated conductor 16' couples to electrode 16, and conductor segment 20' couples to electrode 20. Furthermore, three of the conductors (denoted collectively with reference numeral 24) couple to three cuff-type conductors 25,26,28 adapted to receive proximal portions of medical electrical leads while another three of the conductors couple to conductive pads 25',26',28' which are aligned with, but spaced from the conductors 25,26,28 along a trio of bores (denoted as 25",26",28" in FIG. 4 herein) formed in header 12. The joint 32 between header 12 and shroud 14 can comprise a variety of mechanisms, including an interlocking, partially spring-biased socket-type connection which, in combination with medical adhesive, provides a reliable mechanical coupling.

Another feature of the invention relates to including radio-opaque markers and/or identifiers within and/or on the shroud 14 so that a physician or clinician can readily determine that an IMD is outfitted with an assembly according to this invention. A marker according to this aspect of the invention can include a metallic insert and/or coating having a unique shape, location and/or configuration (e.g., an "M" or the corporate logo for an IMD manufactured by Medtronic, Inc.).

Depicted in FIGS. 5 and 6 is an elongated structural support member 36 which provides a reliable connection to a metallic housing of an IMD (not shown) via traditional processes (e.g., laser welding). The member 36 has a three substantially orthogonal sides (all denoted as 36 in FIGS. 5 and 6) thus providing three discrete bonding areas between the header 12 and an IMD. Of course, the member 36 could be perforated and/or coated with an insulative material, but in the embodiment depicted one side is cut out or not present so that the plurality of conductors 24 can pass from the header 12 and shroud 14 to the feedthrough array of the IMD.

Electrodes 16, 18,20 and/or the (corresponding elongated conductors) can be fabricated out of any appropriate material, including without limitation tantalum, tantalum alloy, titanium, titanium alloy, platinum, platinum alloy, or any of the tantalum, titanium or platinum group of metals whose surface may be treated by sputtering, platinization, ion milling, sintering, etching, or a combination of these processes to create a large specific surface area. Also as noted herein, an electrode can be stamped, drawn, laser cut or machined using electronic discharge apparatus. Some of the foregoing might require de-burring of the periphery of the electrode or alternately any sharp edges due to a burr can be coupled facing toward the corresponding recess in the shroud member thereby minimizing likelihood of any patient discomfort post-implant while further reducing complexity in the fabrication of assemblies according to the invention. The electrodes can be coated or covered with platinum, a platinum-iridium alloy (e.g., 90:10), platinum black, titanium nitride or the like.

Figure 7:
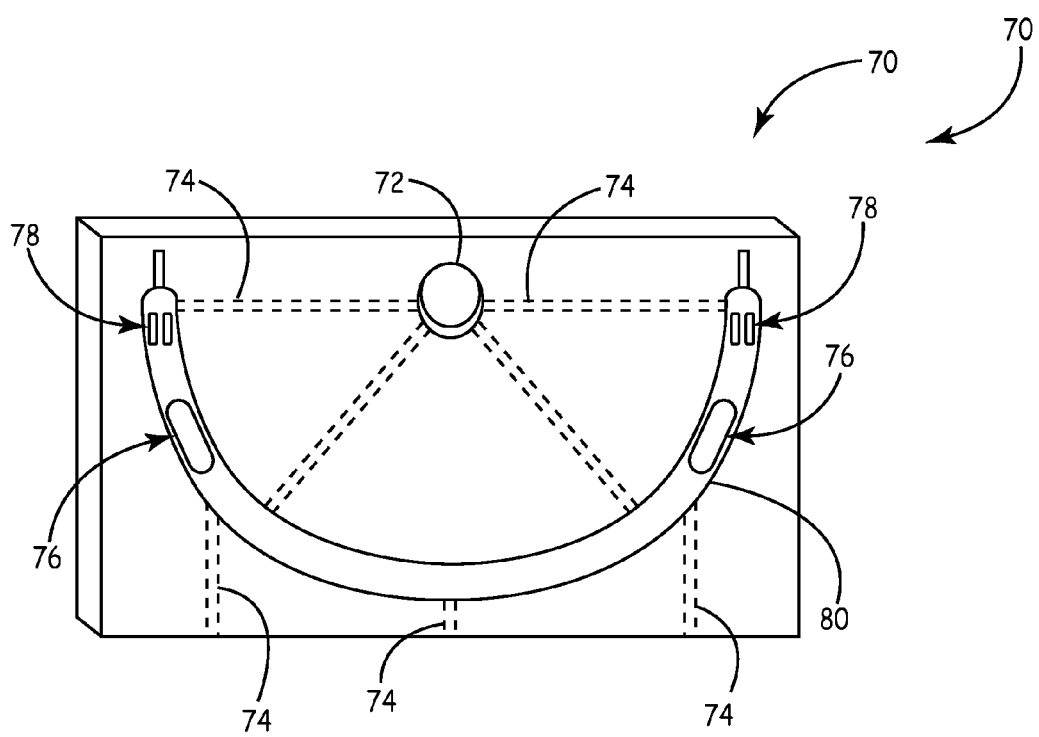
FIG. 7 is a perspective view of certain portions of an exemplary mold used according to the invention for fabricating resilient cardiac activity sensing shroud members for a variety of IMDs.

FIG. 7 is a perspective view of certain portions of an exemplary insert-molding mold 70 used according to the invention for fabricating resilient cardiac activity sensing shroud members for a variety of IMDs. Although only one side of the mold 70 is depicted in FIG. 7, such molds typically include two opposing parts defining a cavity 80 configured to receive an injection molding material. As depicted a nominal primary material receiving port 72 couples to the cavity 80 via a plurality of passages 74. The passages 74 can function as fluid-admitting and/or fluid-exiting features and they are typically arranged to ensure complete filling of the cavity 80 so the article defined by the cavity 80 is fully constituted. Of course, while a nominal primary port 72 is depicted a plurality of ports 72 can be implemented without departing from the disclosure of the invention. Also, the curvilinear shape of the cavity 80 depicted in FIG. 7 is simply for illustration as myriad sized and shaped articles can be fabricated according to the invention. As depicted, the interior of the cavity 80 includes a pair of electrode-receiving structures 76 each said structure corresponds to an optional conductor-receiving structure 78. The structures 76,78 are used to temporarily retain electrodes (not shown) and elongated conductors (not shown) during fabrication of shroud assemblies according to the invention.

Thus, to fabricate said shroud assemblies in a single cavity or a multiple cavity mold the following exemplary steps can be performed. First a mold 70 is provided which is adapted for insert-injection-molding operations. As noted briefly above, the mold 70 includes at least one cavity 80 adapted to receive a biocompatible injection molding material. The mold 70 includes at least one injection molding pathway 72,74 coupling an exterior of the mold 70 to said cavity 80. In one form of the invention, the cavity 80 comprises a substantially curve-shaped hollow portion that includes at least two electrode-receiving structures 76 and a like number of elongated conductor-receiving structures 78. Furthermore, said structures 76,78 cooperate to guide respective conductors to provide electrical communication between an electrode in an electrode-receiving structure 76 and an elongated conductor disposed in a conductor-receiving structure 78. Then, either manually or automatically one temporarily mechanically couples at least two electrodes to the electrode-receiving structures 76 within the cavity 80 of the mold 70. Optionally, one temporarily mechanically couples at least two elongated conductors to the conductor-receiving structures 78 within the cavity 80 of the mold 70. If necessary (for a multi-part mold) the cavity is sealed closed with the components in place.

Then a biocompatible injection-molding material is injected into the cavity 80 in either a precise amount known to completely fill the cavity 80 and thus form the desired multi-component part (i.e., cardiac sensing shroud assembly). Optionally, the mold 70 can be cooled or otherwise temperature treated.

Also, as is known in the art, a release agent can be applied to the cavity 80 and/or imparted into the material prior to or during injection. In addition, one can apply one of a layer of material and a coating on a major planar surface of the electrodes to maintain the sterile manufacture thereof and/or preserve function following chronic implantation.

Finally, the shroud assembly is then coupled around at least a part of the peripheral portion of an IMD such as an implantable cardiac pacemaker, an implantable cardioverter-defibrillator, an implantable fluid delivery device, an implantable neurostimulator, an implantable gastric simulator, and the like.

Accordingly, a number of embodiments and aspects of the invention have been described and depicted although the inventors consider the foregoing as illustrative and not limiting as to the full reach of the invention. That is, the inventors hereby claim all the expressly disclosed and described aspects of the invention as well as those slight variations and insubstantial changes as will occur to those of skill in the art to which the invention is directed. The following claims define the core of the invention and the inventors consider said claims and all equivalents of said claims and limitations thereof to reside squarely within their invention.

The invention claimed is:

1. An apparatus used to fabricate a subcutaneous cardiac activity sensing device, comprising:

a mold having a cavity adapted to receive a biocompatible injection molding material, said mold including at least one injection molding pathway coupling an exterior of the mold to said cavity, wherein said cavity comprises a substantially curve-shaped hollow portion and said cavity includes at least two electrode-receiving structures and a like number of elongated conductor-receiving structures, further wherein said structures cooperate to provide electrical communication between an electrode disposed in an electrode-receiving structure and an elongated conductor disposed in a conductor-receiving structure;

at least two electrodes each configured to temporarily mechanically couple to the electrode-receiving structures;

at least two elongated conductors temporarily mechanically coupled to the conductor-receiving structures;

at least one fluid entrance port configured to receive an initial supply of a biocompatible injection molding material; and at least one fluid exit port configured to receive an excess amount of the biocompatible injection molding material.

2. An apparatus according to claim 1, wherein said molding material comprises a resilient material.

3. An apparatus according to claim 2, further comprising one of a coating and a layer of material disposed on a least one major planar surface portion of one of the at least two electrodes.

4. An apparatus according to claim 3, wherein the at least two electrodes include opposing major planar surfaces and the major planar surfaces mimic a curved portion of the shroud member.

5. An apparatus according to claim 4, wherein a first said opposing major planar surface has a greater surface area than a second said opposing major planar surface.

6. An apparatus according to claim 5, wherein the first said opposing major planar surface couples within an interior surface portion of the shroud member and the second said opposing major plan surface is substantially coplanar with an exterior surface portion of the shroud member.

7. An apparatus according to claim 6, further comprising an implantable medical device (IMD) having a volume of medical adhesive disposed on an exterior surface of the IMD and wherein the shroud member couples to the periphery of the IMD.

8. An apparatus according to claim 7, wherein the IMD comprises one of: an implantable cardiac pacemaker, an implantable cardioverter-defibrillator, an implantable fluid delivery device, an implantable neurostimulator, an implantable gastric simulator.

9. An apparatus according to claim 1, wherein the at least two elongated conductors comprise a structure integrally formed with a respective one of the at least two electrodes.

10. An apparatus according to claim 9, wherein the conductors and the electrodes are fabricated from a common material.

11. An apparatus according to claim 10, wherein the common material comprises one of titanium, platinum, and an alloy of either titanium or platinum.

12. An apparatus according to claim 1, further comprising a mold-release agent disposed within at least a portion of the cavity.

13. An apparatus according to claim 1, wherein the mold comprises one of a multi-part and a multi-cavity injection molding mold.

14. An apparatus according to claim 1, wherein the at least two electrodes are fabricated from one of a titanium material and a platinum material.

15. An apparatus according to claim 14, wherein the at least two electrodes further include a coating on at least a major surface thereof.

16. An apparatus according to claim 15, wherein the coating comprises one of a nitride coating, a carbon black coating, a time-release coating.

17. A device according to claim 1, further comprising medical grade adhesive disposed around between the at least a part of the periphery of the IMD.

18. A method of fabricating a cardiac sensing shroud assembly for an implantable medical device (IMD), comprising:

providing a mold adapted for insert-injection-molding operations
wherein said mold includes a cavity adapted to receive a biocompatible injection molding material and said mold includes at least one injection molding pathway coupling an exterior of the mold to said cavity, wherein said cavity comprises a substantially curve-shaped hollow portion and said cavity includes at least two electrode-receiving structures and a like number of elongated conductor-receiving structures, further wherein said structures cooperate to provide electrical communication between an electrode disposed in an electrode-receiving structure and an elongated conductor disposed in a conductor-receiving structure;

temporarily mechanically coupling at least two electrodes to the electrode-receiving structures within the cavity of the mold;

temporarily mechanically coupling at least two elongated conductors to the conductor-receiving structures within the cavity of the mold; and injecting the biocompatible injection molding material into the cavity.

19. A method according to claim 18, further comprising: applying one of a layer of material and a coating on a major planar surface of the at least two electrodes.

20. A method according to claim 18, further comprising: coupling the shroud member around at least a part of the peripheral portion of the IMD, and wherein the IMD comprises one of: an implantable cardiac pacemaker, an implantable cardioverter-defibrillator, an implantable fluid delivery device, an implantable neurostimulator, an implantable gastric simulator.

* * * * *